(12) United States Patent
Thomas

(10) Patent No.: US 6,242,074 B1
(45) Date of Patent: *Jun. 5, 2001

(54) PROCESS TO MELT BOND FIBERS ONTO THREE-DIMENSIONAL FORMED FILM TO ACHIEVE A CLOTH-LIKE TEXTURE AND THE FILM PRODUCED THEREBY

(75) Inventor: Paul E. Thomas, Terre Haute, IN (US)

(73) Assignee: Tredegar Film Products Corporation, Richmond, VA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/850,635

(22) Filed: May 2, 1997

Related U.S. Application Data

(63) Continuation of application No. 08/395,842, filed on Feb. 28, 1995, now abandoned.

(51) Int. Cl.$^7$ .................................................. B32B 27/12
(52) U.S. Cl. ...................... 428/137; 428/138; 428/297.7; 428/297.4
(58) Field of Search .................................. 442/394, 398; 428/297.7, 297.4, 137, 138, 903

(56) References Cited

U.S. PATENT DOCUMENTS

| | | |
|---|---|---|
| D. 268,962 | 5/1983 | Adams et al. . |
| 3,219,507 | 11/1965 | Penman . |
| 3,765,922 | 10/1973 | Chisholm . |
| 3,871,378 | 3/1975 | Duncan et al. . |
| 3,878,014 | 4/1975 | Melead . |
| 3,929,135 | 12/1975 | Thompson . |
| 3,945,386 | 3/1976 | Anczurowski et al. . |
| 3,967,623 | 7/1976 | Butterworth et al. . |
| 4,041,951 | 8/1977 | Sanford . |
| 4,259,286 | 3/1981 | Louis et al. . |

(List continued on next page.)

FOREIGN PATENT DOCUMENTS

| | | |
|---|---|---|
| 4016348 | * 11/1991 | (DE) . |
| 4016348A1 | 11/1991 | (DE) . |
| 0 403 187 B1 | 8/1990 | (EP) . |
| 53-105573 | 9/1978 | (JP) . |
| WO 92/07121 | 4/1992 | (WO) . |
| WO 93/22995 | 11/1993 | (WO) . |
| WO 94/24354 | 10/1994 | (WO) . |
| WO 9604131 A1 | 2/1996 | (WO) . |
| WO 96/21760 | 7/1996 | (WO) . |

OTHER PUBLICATIONS

H–1827; Cooper et al.; Fibrous and Apertured, Three–Dimensional Macroscopically Expanded Plastic Web; Pub. Jan. 4, 2000.

H–1670; Aziz et al.; Absorbent Article Having a Nonwoven and Apertured Film Coversheet; Pub. Jul. 1, 1997.

European PCT Search Report for PCT/US96/00267 dated May 13, 1996 corresponding to U.S. Ser. No. 08/395,842.

*Primary Examiner*—Elizabeth M. Cole
(74) *Attorney, Agent, or Firm*—Jenkens & Gilchrist, PC

(57) ABSTRACT

A composite material having improved cloth-like texture and fluid transfer properties is disclosed. In one embodiment, the composite material has a polymeric film with a plurality of apertured protuberances and a plurality of loose fibers coupled to the polymeric film, including at least a portion of the sidewalls of the protuberances. In another embodiment, the composite material has a polymeric film with first and second layers, a plurality of apertured protuberances extending through both layers, and a plurality of loose fibers coupled to the first layer and to at least a portion of the sidewalls of the protuberances.

31 Claims, 8 Drawing Sheets

U.S. PATENT DOCUMENTS

| | | |
|---|---|---|
| 4,323,069 | 4/1982 | Ahr ........................................ 128/287 |
| 4,324,246 | 4/1982 | Mullane et al. . |
| 4,327,730 | 5/1982 | Sorensen . |
| 4,342,314 | 8/1982 | Radel et al. . |
| 4,351,784 | 9/1982 | Thomas et al. . |
| 4,463,045 | 7/1984 | Ahr et al. . |
| 4,508,256 | 4/1985 | Radel et al. . |
| 4,541,794 | 9/1985 | Raley et al. . |
| 4,552,709 | 11/1985 | Koger, II et al. . |
| 4,629,643 | 12/1986 | Curro et al. . |
| 4,652,484 | 3/1987 | Shiba et al. . |
| 4,741,877 | 5/1988 | Mullane, Jr. . |
| 4,772,444 | 9/1988 | Curro et al. . |
| 4,878,825 | 11/1989 | Mullane, Jr. . |
| 4,963,392 | 10/1990 | Molnar et al. . |
| 4,995,930 | 2/1991 | Merz ...................................... 156/209 |
| 5,158,819 | 10/1992 | Goodman, Jr. et al. . |
| 5,171,238 | 12/1992 | Kajander . |
| 5,180,620 | 1/1993 | Mende . |
| 5,190,812 | 3/1993 | Joseph ................................... 428/297 |
| 5,295,986 * | 3/1994 | Zehner et al. ..................... 604/385.1 |
| 5,332,613 | 7/1994 | Taylor ................................... 428/152 |
| 5,366,453 | 11/1994 | Zehner et al. . |
| 5,368,910 | 11/1994 | Langdon .............................. 428/137 |
| 5,514,470 | 5/1996 | Haffner ................................. 428/246 |
| 5,536,555 | 7/1996 | Zelazoski ............................. 428/138 |
| 5,885,681 | 3/1999 | Korpman .............................. 428/68 |
| 5,962,106 | 10/1999 | De Carvalho et al. .............. 428/131 |

\* cited by examiner

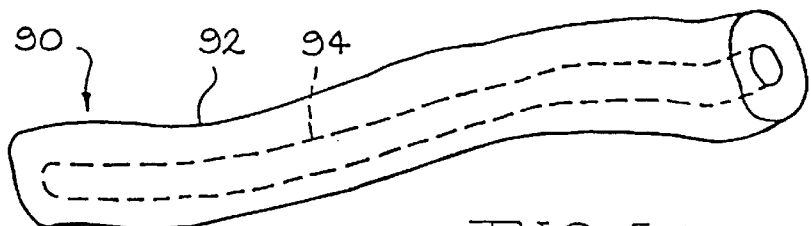
FIG. 5A
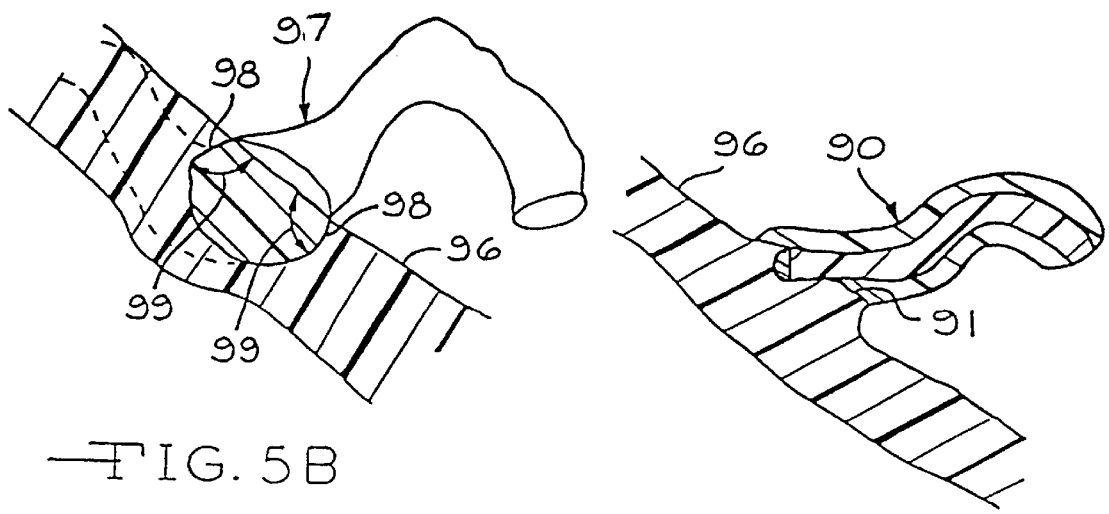
FIG. 5B
FIG. 5C
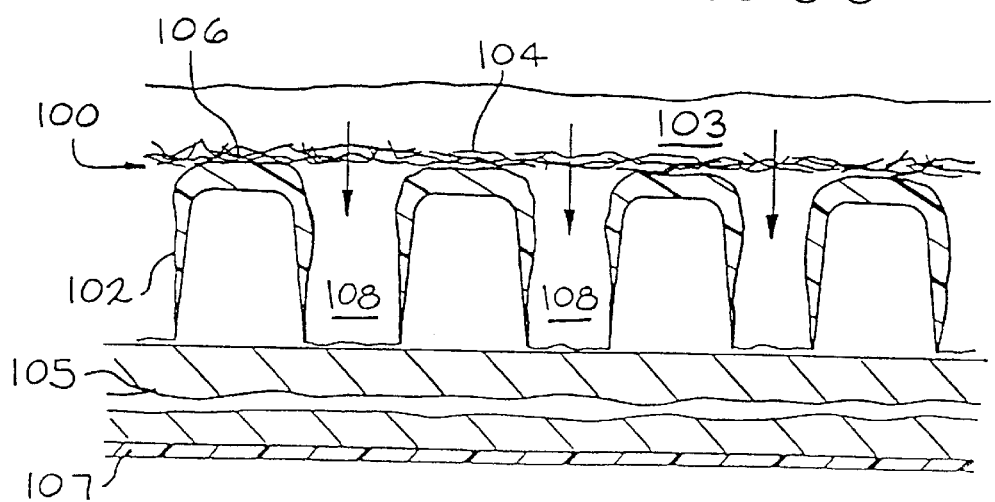
FIG. 6

(NOT TO SCALE)

PROCESS TO MELT BOND FIBERS ONTO THREE-DIMENSIONAL FORMED FILM TO ACHIEVE A CLOTH-LIKE TEXTURE AND THE FILM PRODUCED THEREBY

This is a continuation of copending application(s) Ser. No. 08/395,842 filed on Feb. 28, 1995, now abandoned.

TECHNICAL FIELD

The present invention relates to a process for melt bonding fibers onto formed films to achieve a cloth-like texture. The resulting product is useful in a disposable product, for example, as topsheets in diapers and hygiene products.

BACKGROUND OF THE INVENTION

Absorbent articles such as sanitary napkins, incontinent devices, diapers, wound dressings and other products are well known. These articles absorb liquid and retain the liquid within a core. The interior or topsheet of the absorbent article is made of a flexible plastic film material. Many attempts have been made to overcome the negative characteristics of the glossy or "plastic" look and sticky tactile feel to the plastic films. It is therefore desirable to produce absorbent devices which have a cloth-like look and feel to a user's skin.

Many types of films have been proposed to overcome these tactile problems, including the use of microapertured polymeric webs. Various types of formed or perforated films and processes for making formed films are disclosed in: U.S. Pat. Nos. 3,871,378; 3,929,135; 4,041,951; 4,259,286; 4,323,069; 4,324,246; 4,327,730; 4,342,314; 4,351,784; 4,463,045; 4,508,256; 4,541,794; 4,552,709; 4,629,643; 4,741,877; 4,772,444; 4,878,825; 5,158,819 and Des. 268,962 which depict a variety of absorbent articles using cell shapes and surface texturing or aperturing techniques aimed at providing a film having the desired aesthetic characteristics.

While these films allow fluid passage therethrough, there is a considerable top surface area which does not allow passage of fluid through the film onto an absorbent core below. Thus, the areas of film between the apertures still adhere to the wearer's skin, especially when there is liquid present. This adherence also results in a sticky or plastic perception against the wearer's skin.

Another attempt to overcome the disadvantages of plastic films involves the use of flocked films, where adhesives are used to bond fibrils and/or fibers to a plastic film. However, the application and handling of the adhesive material onto a formed perforated film has many disadvantages. It is difficult to uniformly apply the adhesive to the formed film layer such that the fibers adequately adhere to the film. The fibers tend to rub off and produce "lint" on the wearer. Further, the adhesive materials, whether aqueous or solvent-based, bring additional chemicals into direct contact with the wearer's skin. These adhesives sometimes result in allergic and/or sensitive reactions, such as diaper rash. In addition, the environmental concerns of handling, application and recovery of the volatile materials in the adhesive materials must be addressed.

Another attempt to overcome the disadvantages of plastic films involved a process wherein thick layers of fibers are laminated to plastic films by pulling the fibrous webs under tension, for example, U.S. Pat. No. 4,995,930 and German DE 40-16-348-A1. However, these processes have drawbacks in that only thick layers of fibrous material can withstand the applied tension and maintain their web integrity while being laminated to a plastic film. However, in many end uses it is undesirable to have thick layers of fibers on the plastic film. Thick layers of fibrous webs will retard the flow rate of fluid into the absorptive device. They will also, by their dense mass of fibers, retain fluids within themselves by capillary retention. This will yield a sensation of wetness to the user. Both of these negative attributes of prior art are overcome by the present invention.

Accordingly, it is one object of the present invention to provide a formed film having a thin layer of fibers adhered thereto, which film has an aesthetically desirable cloth-like look and tactile feel.

It is another object of the present invention to provide a cloth-like three-dimensional fibrous coated polymeric material which does not produce perceptible noise typically associated with plastics when worn by a user.

Another object of the present invention is to provide a three-dimensional fibrous coated polymeric material which is suitable for use disposable absorbent product, such as diapers, catamenial pads and adult incontinent products and wound dressings.

Another object of the present invention is to provide a method and apparatus for producing three-dimensional polymeric webs coated with a fibrous material that is so light and thin that it cannot maintain its own integrity under tension.

DISCLOSURE OF THE INVENTION

The present invention relates to surface-modified perforated or formed polymeric films, wherein a fibrous material is applied to a formed or three-dimensional polymeric film without the use of adhesive materials. The fibrous material can comprise loose fibers, fibrous webs, woven or non-woven materials. In one embodiment, a thin layer of the fibrous material is melt bonded to a top surface of the molten or semi-molten film material at a point in time prior to forming the three-dimensional structure of the film.

The fibrous coated film of the present invention combines the advantages of increased fluid acquisition and dryness, as well as the cloth-like surface feel of cloth or non-woven materials. The resulting surface-modified formed film has a suede or cloth-like texture and surprisingly provides increased fluid acquisition to a product incorporating such formed film. The film of the present invention is especially useful as an absorbent product topsheet material.

The use of hydrophobic fibers results in a soft feel and a dull, fibrous look without capillary wetting at the liquid acquisition surface of the fibrous coated formed film. The fibrous surface on the formed film can be achieved using one or a combination of fiber transfer processes, including fiber air laying, fiber carding, melt blowing, fiber dusting, flocking or a spun bond process.

According to the present invention, a predetermined amount of a fibrous material is introduced onto a top surface of a film material just prior to or directly at the point of forming the three-dimensional structure of the film. In preferred embodiments, the film is formed into a three-dimensional structure using a vacuum or pressure differential process. The fibrous material covers a predetermined area of the film surface and embeds or fuses onto the top surface of the film. One embodiment of the present invention uses an air-layed or carding process such that the fibrous material is transferred to the surface of the film by a conveyor belt system. Another embodiment uses a melt blown process such that the fibrous material is directly applied to a top surface of the film at the point in time prior to the formation of the three-dimensional structure of the film.

The fibrous material can comprise either loose fibers or lightweight webs of fibrous material. One advantage of the present invention is that a uniformly thin layer of fibrous material can be applied to a film during the film making process. Until the present invention, it has not been possible to supply a thin layer of fibrous material under low to minimal tension (and in certain embodiments, at near zero tension) onto a film being formed. In particular, attempts to supply lightweight webs onto films were unsuccessful since the lightweight fibrous webs break under tension and lose their web integrity. Until the present invention, it has not been possible to simultaneously supply a lightweight fibrous material onto a film during a process for making a formed or three-dimensional film.

The lightweight material is supplied under zero or near zero tension applied to the fibrous material. There are sufficient forces present to keep a continuous supply of fibrous material being continuously applied onto the film material. These forces are such that the integrity of the fibrous material is not destroyed during the application of the lightweight fibrous material onto the film.

The resulting film has the aesthetic appeal of cloth-like fabrics. Further, the film has the dryness aspect of three-dimensional formed films and allows ready fluid acquisition over the prior art formed films. According to the present invention, it is now possible to apply loose, non-bonded or entangled fibers and/or thin layers of fibrous webs onto a three-dimensional film.

According to preferred embodiments, the process involves a precise control of the thermal energies of both the molten or semi-molten polymer film and the fibers at the point in time prior to when the molten polymer film is subjected to the pressure differential forming the three-dimensional structure to the film. The thermal energy is controlled such that the heat transfer (which is required to achieve the bond between film and fiber) does not detract from the ability of the film to be further formed into its three-dimensional structure. The fibers are dispensed onto a top surface of the film being formed. The fibrous materials become embedded or infused into/onto the film's top surface without distortion or loss of the fiber's integrity as a fiber. The fibers embed or fuse as the three-dimensional structure of the film is being formed such that a fibrous coated three-dimensional formed film is produced. The resulting film has increased aesthetic value due to the looseness of the ends of the fibers.

The present invention also depends, in part, on the precise location or impingement point at which the fibrous materials are delivered onto the top of the molten film material. The fibrous materials are delivered onto the molten film material at a point prior to the three-dimensional structure of the film being formed. In a preferred embodiment the three-dimensional structure of the film is formed by subjecting a bottom surface of the molten film to a pressure differential. The precise location or impingement point of fiber to film is such that various operating conditions are met. The contact temperature and contact pressure between the fibrous material and the molten film material are regulated. The location of impingement of fibers onto film is regulated such that the fibers do not touch the molten film material prematurely, but only at a desired impingement location (which, in preferred embodiments, is at a predetermined distance from the point that the pressure differential is supplied to the film). The fiber delivery location is regulated such that the fibers or fibrous materials are delivered to the top of the molten film material without interfering with the formation of the three-dimensional structure of the film. The pressure differential being used to form the three-dimensional structures on the film is regulated. In a preferred embodiment, the fibers are supplied onto the film in a manner such that there is minimal, if any, obstruction or resistance to the air flow or to the pressure differential being used to form the three-dimensional structure of the film.

The process of the present invention regulates the thermal energy of the polymeric film as the film progresses across the pressure differential. Enough heat is retained such that the fibrous coated film is molten for a sufficient time in order to form the three-dimensionally expanded protuberances, apertures or ruptures in the film. Thereafter, sufficient heat is removed (to a point below the temperature of crystallization (Tc)) before the fibrous coated film is removed from the pressure differential.

Sufficient pressure differential is maintained to cause the three-dimensional structures such as protuberances and/or apertures to be formed in the fibrous coated polymeric film. The fibrous materials supply additional resistance to the fluid or air displacement across the pressure differential. The amount of pressure differential is regulated to compensate for the additional resistance resulting from the presence of the fibrous materials now affixed to the top side of the polymeric webs as fibrous coated film web passes across the pressure differential.

The present invention can be practiced using either a batch process using pre-made rolls of fibrous webs or using a continuous supply of individual fibers or fibrous webs introduced onto the film material. The present invention thus allows for very lightweight uniform layers of fibers or fibrous webs to be adhered to a three-dimensional formed film.

In certain embodiments, selective coverage of the film with the fibrous material is achieved by transferring the fibrous material to a predetermined area on the film in a selected pattern. In the process where non-woven fibrous materials are used, the non-woven fibrous material is slit, unwound and delivered or channeled over the selected areas of the film. Fibrous material useful in the process of the present invention can include polyesters, polyolefins, acrylics, rayons, cottons or blends of the same. The fibrous material can also include bicomponent and adhesive fibers, as well as fibers having different geometries, lengths, diameters and surface finishes. The fibrous material and non-woven materials can have different basis weights, fiber compositions, fiber lengths and be made using different processes.

BRIEF DESCRIPTION OF THE DRAWINGS

FIG. 5A is a greatly enlarged, simplified cross-sectional schematic illustration of a coextruded fiber.

FIG. 5B is a greatly enlarged, simplified cross-sectional schematic illustration of a fiber mechanically bonded to a film.

FIG. 5C is a greatly enlarged, simplified cross-sectional schematic illustration of a coextruded fiber fused to a film.

FIG. 6 is a greatly enlarged, simplified cross-sectional schematic illustration of a fibrous coated formed film having a three-dimensional perforated film layer and a non-woven fibrous material layer.

DETAILED DESCRIPTION OF THE PRESENT INVENTION

The present invention relates to a surface-modified perforated or formed film which is particularly useful as a topsheet for absorbent products, such as catamenial pads, disposable diapers, adult incontinent products, wound dressings and the like. However, the present invention is not limited to such applications and the film of the present invention may be used advantageously to produce other products comprising a plastic film having desired cloth-like tactile characteristics. For ease of illustration, a surface modified formed film comprising a fibrous coated three-dimensional polymeric web which useful for topsheets in a disposable absorbent product is described. However, this detailed description will allow those skilled in the art to adapt this invention to produce surface modified formed film for other applications.

Figure 1:
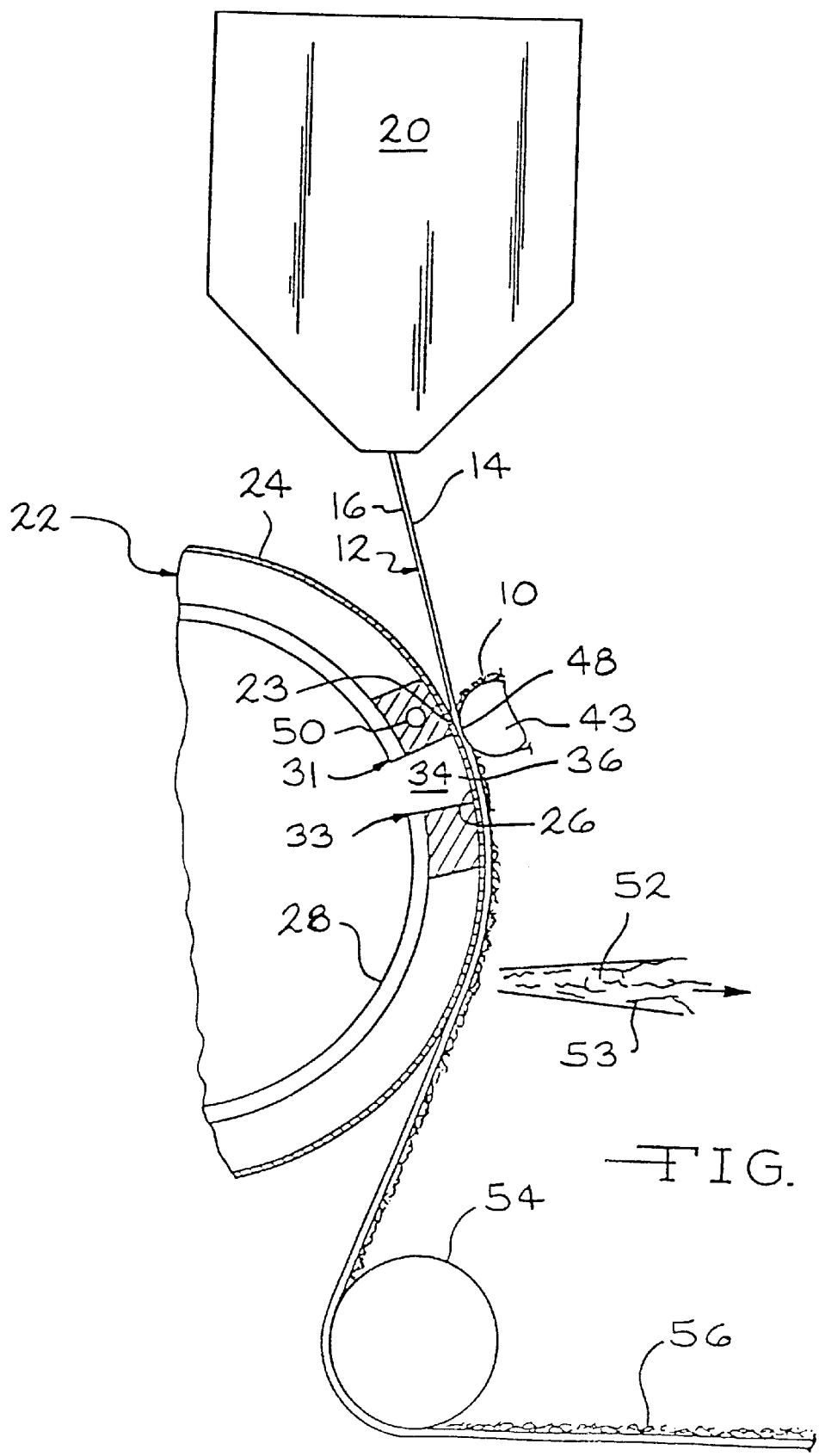
FIG. 1 is a simplified cross-sectional schematic illustration of a process for producing a fibrous coated formed or perforated film.

FIG. 1 is a simplified schematic diagram showing a process to adhere a predetermined amount of a lightweight fibrous material onto a polymeric film to achieve a cloth-like texture on the film. Fibrous material 10 is applied over nip roll 43 to a molten or semi-molten polymeric web or film 12 having a top surface 14 and a bottom surface 16. In the embodiments shown, the film 12 is dispensed from a film die 20, preferably at a distance of about 2 to about 10 inches and most preferably about 3 to about 4 inches from a point of contact 23 on a screen or film forming means 22. The film material 12 is delivered at an elevated temperature as a molten or semi-molten plastic or polymer resin mass, and in certain embodiments is delivered at a temperature of about 350 to 600° F. (175° C.–315° C.). The film material 12 is formed and perforated by passing the stream of the film material 12 over the film forming means 22 and a pressure differential means 23. It is to be understood that the film forming means 22 can be a conveyor belt type of apparatus (not shown) or other pressure differential means which moves the film material 12. For the ease of illustration, the film forming means 22 is depicted herein as a screen or drum. The film forming means 22 has a rotating surface 24 which is highly perforated with a plurality of apertures 26 extending therethrough. The apertures 26 can be randomly spaced on the surface 24 or can form a predetermined pattern for aesthetic and/or functional requirements. The apertures 26 allow a fluid such as air to pass through the surface 24 of the film forming means 22. The film forming means 22 generally includes a leading edge of a seal 31 and trailing edge of a seal 33 which define a vacuum chamber 34. In certain preferred embodiments, the distance between the seals 31 and 33 ranges from about 25 to about 6 inches and in certain embodiments is about 1.5 inches. When the film forming means 22 is a screen, as shown in the figures herein, it is preferred that the perforated surface 24 rotate over the seals 31 and 33. The vacuum chamber 34 is located within the film forming means 22 and is utilized to create a pressure differential between the top surface 14 and the bottom surface 16 of the film 12.

As the film 12 is extruded from the die 20, the film 12 comes into contact with the rotating perforated surface 24 of the film forming means 22. The rotating perforated surface 24 of the film forming means 22 moves continuous portions of the film 12 across the vacuum chamber 34. The pressure differential caused by the vacuum chamber 34 pulls portions of the film 12 which are adjacent the apertures 26 in the surface of the screen 24 into the apertures 26 and causes a plurality of three-dimensional structures or apertures 36 to form in the film 12 at the points adjacent the apertures 26 in the screen 24.

In the process shown in FIG. 1, the fibrous material 10 can be metered and controlled or calendared to a desired density and layered thickness. In certain embodiments, it is advantageous to use random loose fibers in a continuous process which feeds the loose fibers onto the film. In other embodiments, it is advantageous to use lightweight non-woven web materials which are supplied onto the film at zero or near zero tension.

It is to be understood that the present invention is especially useful in applying fibrous material which comprise loose individual fibers and microfibers (i.e., which are not bonded or entangled together) and for applying lightweight webs of fibers having a uniform density thickness and basis weight, yet too light to maintain their web integrity under tension. In various embodiments, the fibrous material 10 is very fragile and is transferred to the film 12 under almost no tension to avoid breakage of the fibrous material 10.

Referring again to FIG. 1, a dispensing means 40 transfers the fibrous material 10 to an impingement or lamination point 48 where the fibrous material 10 and the stream of film 12 contact each other.

The fibrous material 10 contacts the film 12 at a point prior to the leading edge 31 defining the vacuum chamber 34. In a preferred. embodiment, a temperature control means 50 is positioned inside leading edge seal 31 at a point near where the fibrous material 10 contacts the film 12. In the embodiment shown, the temperature control means 50 is shown as a rod heater. Impingement roll 43 can also be temperature controlled to add heat or cooling as desired. However, it is to be understood that other temperature control means, including other heating means or cooling means, can be used to adjust the temperature of the film 12 and fibrous material 10 at this point. The fibrous web material 10 embeds partially into and/or melt fuses onto the film 12. In certain embodiments, the temperature control means 50 and impingement roll 43 are adjusted to achieve the correct balance of heat to the film 12 and the fibrous material 10 to counteract any negative heat flux in the film 12 which occurs when the fibrous material 10 contacts the film 12. The heat supplied from these temperature control means ensures good bonding of the fibrous material 10 to the film 12. The film 12 and the fibrous material 10 are then delivered to the vacuum chamber 34 at an optimum temperature to enable the three-dimensional structures or apertures 36 to be formed in the film 12 as portions of the fibrous coated film 12 move across the vacuum chamber 34.

The temperature at the point of lamination of fibrous material 10 to film 12 is regulated such that the fibrous material 10 adheres to the film 12 while providing the film 12 with a soft cloth or suede-like surface texture.

According to the present invention, the fibrous material adheres to the polymeric film substrate without the use of adhesives. The molten state of the film is maintained such that the film can be readily formed into a three-dimensional formed film. The film material is molten which means that the thermoplastic melt stream of the film material is at a temperature above the temperature of melting ($T_m$) of the thermoplastic film material. The temperature of melting of polymers is determined on a Differential Scanning Calorimeter. When the polymer stream is in the molten phase, the polymer is amorphous; that is, molecules are free to move about, particularly when influenced by outside forces such as a pressure differential. Once the polymer film has been moved by the pressure differential force and has conformed to the shape of the aperture 26 in the surface 24 of the pressure differential means 22 while over vacuum chamber 34, the polymer film is held in that shape until the polymer becomes set or mostly crystallizes. At that time, the film is no longer formable and the film retains its new shape with the three-dimensional structure therein. This phase is known as the temperature of crystallinity (Tc) and is also determined by a Differential Scanning Calorimeter.

The polymer film stream is above the temperature of melting for a sufficient period of time to form the three-dimensional structure or aperture while under the influence of the pressure differential. After the three-dimensional structure or aperture is formed, the polymer film releases enough heat to move below the temperature of crystallinity while still being held in its new shape by the pressure differential.

The addition (or removal) of heat at the point of impingement (lamination) between the fibrous material and the polymer film stream enhances the mechanical bonding and melt fusing by adding a positive (or negative) heat flux to counteract the negative (or positive) heat flux caused by the contact of the polymeric melt stream with the fibrous material. It is also contemplated that heat can be added or removed from the fibrous material itself. The amount of heat supplied to or removed from the polymeric film and the fibrous material is dependent upon both the mass of the film and the fibrous material and the heat retention qualities of the film and the fibrous material.

The present invention solves a problem typically found in film forming processes by applying (or removing) heat at the leading edge of the vacuum seal. The film polymer web must be formable, which means that the film must be hot enough to be able to be formed (or perforated). If heat is prematurely removed from the film before the pressure differential is applied to the film to form the three-dimensional structures or apertures in the film, the three-dimensional structures of the film cannot be formed successfully. When a room temperature fibrous material is introduced onto the film at a predetermined point in the film forming process, the fibrous material introduces a negative heat flux which pulls heat out of the polymeric film. The negative heat flux is detrimental to the formation of the film. According to the present invention, the correct heat energy balance is maintained for both fusing or encapsulating the fibrous material onto the top surface of the film and for maintaining the elevated temperature needed to form the film.

According to a preferred process of the present invention the fibers do not remove a significant amount of heat from the polymeric film material 12. Thus, the temperature at the point of impingement and the amount of additional heat (if any) are carefully controlled. The temperature of crystallinity of the fibrous material is higher than the temperature of crystallinity of the film material. The temperature of the film is controlled so that the temperature of the film does not rise beyond the temperature of crystallinity (Tc) of the fibers. Otherwise, the fibers will warp and melt and the resulting product will lose its fiber aesthetics. In many embodiments, the Tc of the fibers is in the range of about 480° F. while the Tc of the thermoplastic film material is in the range of about 220° F. In addition, the temperature of the film is controlled to compensate for heat loss occurring in the film material during the time from which the film material 12 leaves the die to the time when the film material contacts the screen 24. When the molten film material contacts the screen 24 there is a rapid heat transfer from the film to the screen 24 and, when fibers are brought onto the film, additional heat loss occurs. The heat loss or transfer from the film is sufficient to allow the fibers to adhere to the film without any adhesive, but the heat loss is not too great such that three-dimensional structures can be formed when the film material passes over the pressure differential and the vacuum further cools the film and simultaneously forms the three-dimensional structures on the film material.

Since the fibers have removed heat from the molten film material and act as resistors to air flow, more air or a greater pressure differential is drawn across the vacuum chamber 34 of means 22 in order to form and cool the film material 12. The vacuum pressure depends on the thickness of the layer of fibers being applied to the top of the formed film. In preferred embodiments, between about 10 to about 20% more air is drawn across the vacuum when the fibers are on the film versus when only a non-fibrous coated film is being formed as in prior art. This fluid volume is regulated such that the film is cooled to allow formation of the three-dimensional structures without removing heat from the screen. Too much heat removed from the screen will cause the film material on the screen to cool too rapidly, thus preventing good embedment of the fibers on the surface of the film and further preventing the three-dimensional structures or apertures from being formed in the film.

Referring again to FIG. 1, the impingement roll 43 in certain embodiments has a preferred diameter. If the impingement roll 43 has too large a diameter, the impingement roll 43 may either block needed air flow into the vacuum slot 34, or will further cause the fibers 10 to touch the molten film material 12 too early or both. The fibers 10 are not be introduced too early onto the molten material 12 such that the fibers 10 do not melt together or embed too deeply into the film. The fibers 10 are not be introduced too late into the melt stream of the film material 12 such that the film cools too early and the fibers do not bond to the film material 12. Further, in certain embodiments, the impingement roll 43 provides sufficient pressure to help embed the fibers 10 into the film 12 at the impingement point.

The fibers 10 impinge on the top surface 14 of the film material 12 and are embedded in the top surface 14 of the film material 12 just prior to the film being subjected to the vacuum or pressure differential. Therefore, the vacuum does not embed the fibers into the film. Rather, the thermal dynamics of the impingement of the fibers onto the film allows the fibers to be embedded into the surface of the film.

In certain embodiments, a fiber recirculating means 52 can be positioned at a point beyond the trailing seal 32 of the vacuum chamber 34. In the embodiment shown, the fiber recirculating means 52 is a vacuum slot which removes loose or residual fibers 53 that did not bond to the film 12. The pressure differential caused by the recirculating means 52 can also act to bulk or fluff the fibrous material 10 that is bonded to the perforated film 12. Any excess fibers 53 are collected and recycled in an appropriate manner. In embodiments where the fibrous material 10 comprises loose fibers, the excess fibers 53 can be recirculated directly into a source fiber feed (not shown). Alternatively, if the fibrous material 10 is a mat or web, it is contemplated that such excess fibers can be reused in an appropriate manner. At least one further roller 54 can be provided to aid in removing the successive portions of the fibrous formed film 56 from the film forming means 22. In certain embodiments, it is contemplated that the roller 54 can be a cooling roller to remove residual latent heat from the fibrous formed film 56.

According to the present invention, there is lamination of the fibrous material 10 to the material 12 before the film 12 enters the vacuum chamber 34 or is subjected to the pressure differential such that the resulting formed film 56 has a cloth-like texture on the surface of the formed film. The fibrous material 10 is adhered to the film 12 without covering any pattern that is formed on the top surface of the film by the three-dimensional structures 36.

When the three-dimensional hydrophobic polymeric film of the present invention is used as a topsheet in an absorbent product, there is good fluid acquisition by the topsheet. Fluid is allowed to readily pass from the top surface to the bottom surface of the topsheet. The three-dimensional structure of the film of the present invention effectively prevents fluid from being transmitted back to the top surface of the film and next to the wearer's skin. The random loose ends of the affixed fibrous material on the top surface give the film a softness of touch and dullness to the eye previously only found with cloth fabrics.

Figure 2:
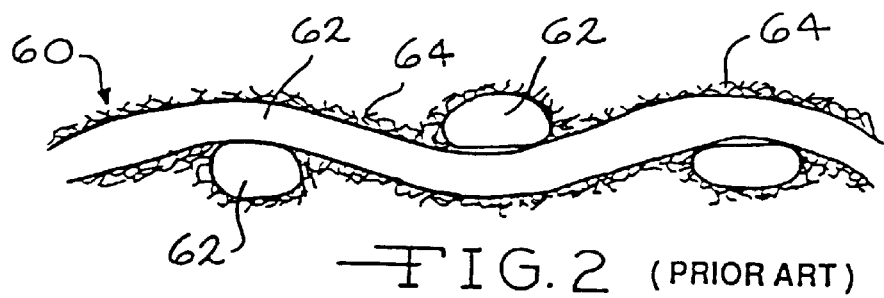
FIG. 2 is a greatly enlarged simplified cross-sectional schematic illustration of a prior art cotton cloth material.
Figure 3:
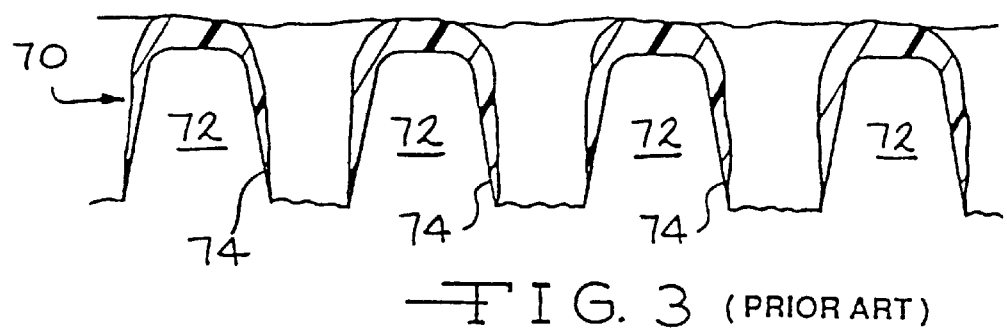
FIG. 3 is a greatly enlarged simplified cross-sectional schematic illustration of a prior art three-dimensional perforated film.

FIGS. 2–3 are simplified cross-sectional schematic illustrations of prior art materials. FIG. 2 shows an enlargement of a prior art cloth diaper depicting the preferred aesthetics of how the cloth material looks and feels. The cloth 60 is made of threads 62 which thread 62 is made of twisted and entangled fibers 64. The look and feel of the desired attributes associated with cloth are derived from the microscopic loose ends of the fibers 64 which protrude randomly from the threads 62 within the weave of the cloth 60. While cloth diapers give the desired softness to the touch when dry and dullness to the eye which yields the perception of softness, when a baby wets the diaper, the capillary action of the threads 62 and fibers 64 (which is common to all cotton cloth materials) maintains a wetness that is undesirable.

FIG. 3 shows an enlargement of a prior art three-dimensional formed or perforated film 70 which is commonly used in catamenial products and is well accepted by the consumer. The film 70 generally comprises microapertures 72 defined by portions of film 74. While the film 70 resolves the wetness functionality problems associated with cloth, the film 70 introduces a negative characteristic with respect to the softness and dullness of the material. It has been found that while women consider a film 70 (such as is shown in FIG. 3 as suitable for use in catamenial products, the same consumers will not find it acceptable for a baby product since the film does not look or feel soft. When consumers consider such a film as a diaper topsheet which will come into contact with a baby's skin, it is perceived as being glossy or slick to the touch and having a plastic appearance which is not acceptable. This perception persists even though such a film as shown in FIG. 3 is better for the child in that such film is drier and there is less chance for wetness remaining adjacent the skin.

Figure 4A:
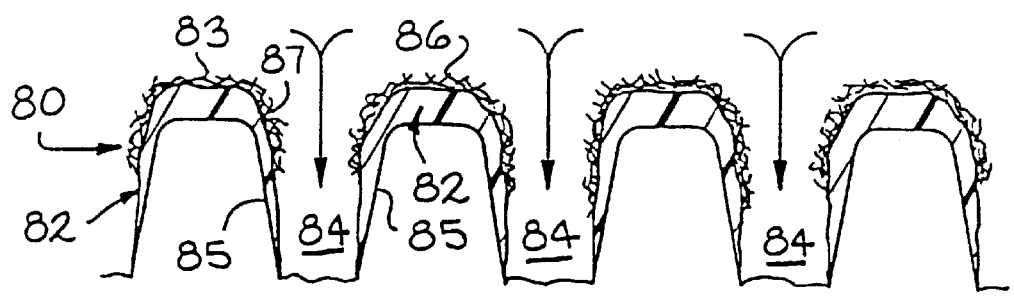
FIG. 4A is a greatly enlarged simplified cross-sectional schematic illustration of a three-dimensional formed film coated with individual fibrils.
Figure 4B:
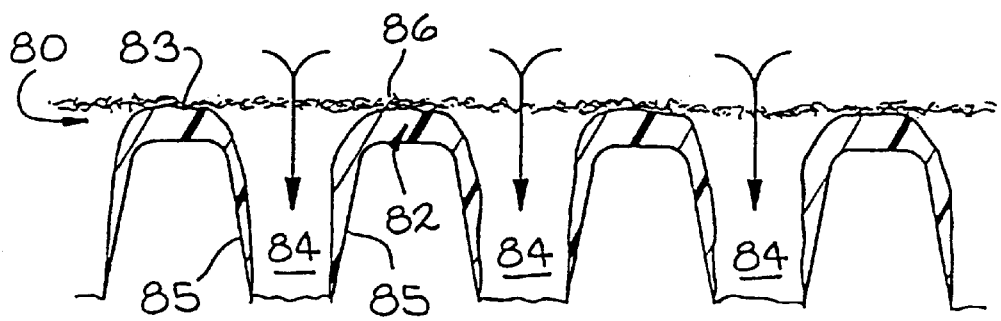
FIG. 4B is a greatly enlarged simplified cross-sectional schematic illustration of a three-dimensional formed film coated with a fibrous web.

FIGS. 4A and 4B are simplified enlarged cross-sectional illustration of two embodiments of a fibrous coated film 80 of the present invention produced according to the method described above. The fibrous coated film 80 solves the issues of both superior dryness functionality and the tactile requirements of softness to the touch and dullness to the appearance. The present invention incorporates the attributes of random loose fibers onto the surface of the microapertured film. The fibrous coated film 80 comprises a microapertured polymeric film layer 82 which has planar surface 83 and a plurality of apertures 84. Each aperture 84 is defined by side walls 85. It is noted that the walls 85 taper from the surface 83 toward the aperture 84 itself. The side walls 85 have a progressively thinning cross-section which is due to the stretching or deformation caused by the pressure differential on the film as the film is moved across the vacuum chamber. Fibrous material 86 is present on the polymeric film layer 82. The fibrous material 86 fuses and/or mechanically bonds to the film layer 82. In certain embodiments, depicted in FIG. 4A, portions 87 of the fibrous material 86 are at least partially pulled against the side walls 85 of the apertures 84. An as depicted in FIG. 4A, a substantial portion of the apertures 84 are not bridged by the fibrous material 86. The apertures 84 thus remain open for the passage of fluids therethrough. The fibrous coated film 80 shown in FIG. 4A allows more readily for the acquisition of fluids and in particular can accommodate more viscous fluids such as found in menses and/or loose bowel movements.

Referring now to FIGS. 5A–5C, some types of polymers readily stick to or adhere to each other while other polymers do not. Typically, the polymers used to make fibrous materials (such as woven or non-woven webs) are very different from the polymers used to make film. The fiber industry typically makes fibers using. polypropylene and/or polyester while films are generally made with polyethylene. However, polypropylene and polyester do not generally adhere to polyethylene without some form of bonding agent between them. By supplying the polypropylene or polyethylene fibrous material onto a hot melt stream of a polymeric film web at a point where the film is still molten, a mechanical lock of the fibrous material on the film occurs. A sufficient amount of the polymeric film flows around the fiber to encapsulate the fiber and adhere it to the film. It is contemplated that the fibrous material can comprise a fibrous material made of one type of polymer or, alternatively, can comprise coextruded fibers to form a fibrous material.

Various types of resin are especially useful in forming the melt blown fibers. One example of a resin used to make melt blown fibers is an 800MFR polypropylene fiber grade resin made by Himont. Also, blends of polypropylene with polyethylene or polyethylene alone, fibers can be utilized in the present invention.

Corona treatment and other such treatments can be practiced with the process of the present invention.

FIG. 5A is a greatly enlarged simplified cross-sectional schematic illustration of a coextruded fiber 90 having an outer or lading layer 92 substantially surrounding an inner or core layer 94. In a preferred embodiment, the outer layer 92 comprises a low melt temperature polymer which preferably melts at the same temperature at which the polymeric film is molten and the inner or core layer 94 comprises a polymer having a significantly higher melting point than the outer layer 92. FIG. 5B shows a monofilament fiber 90 which is mechanically embedded into a film 96. At the point of contact or impingement of the fibrous material onto a molten film stream 96 in the formed film making process, fiber 90 is embedded into the molten film polymer, thereby mechanically bonding the fiber 90 to the film. The fiber's integrity and form are maintained due to its higher melting point such that it does not melt under the same thermal load.

During the process of the present invention, the film is in a molten state which allows fiber 90 to be pushed into the film. The fiber is bonded to the film by a mechanical bond. The mechanical bond between the fiber and film occurs wherein at least the portion 98 of the fiber 90 is positioned within the film 96 at an angle 99 greater than 90°. By achieving an angle greater than 90°, the polymer of the film has achieved a "wrap-around" effect which in effect "clamps" onto the fiber and holds it firmly. It has been surprisingly shown that when a fiber is mechanically bonded to a film at the angle 99 greater than 90°, there is a good mechanical bond between the fiber and the film which has previously not been achieved.

FIG. 5C shows the coextruded fiber 90 melted or fused to the film 96. A portion 91 of the coextruded fiber 90 fuses into the top surface of the film 96. It is contemplated that according to this process, that fibers may be mechanically bonded and/or adhesively fused to the film. Both the mechanical bonding and fusion bonding of fiber-to-film provides a fibrous coated film having a surface with enhanced cloth-like tactile qualities and visual dullness.

Referring now to FIG. 6, the present invention further solves the problem of fluid acquisition, which is the ability of fluids to pass through the topsheet film into an absorbent core. When a fibrous material such as a non-woven material is used in the method of the present invention, the bonded fiber web (while maintaining its web and form) still allows for the production of apertures and for passage of fluid through the apertures. Pressure differential supplied at an appropriate level provides the adequate force necessary to achieve good aperture formation in the fibrous coated material and a topsheet material having desirable fluid acquisition and aesthetic properties. FIG. 6 is a greatly enlarged simplified cross-sectional schematic illustration of an embodiment of a fibrous coated formed film 100 having a microapertured film layer 102 and a non-woven fibrous material layer 104. The microapertured film 102 generally comprises planar surfaces 106 and apertures 108. The non-woven fibrous material layer 104 maintains its integrity and does not extend within the microapertures 108. Fluids 103 pass through the non-woven fibrous material layer 104 and the apertures 108 onto an absorbent core 105 and a fluid impervious backsheet 107.

In preferred embodiments, the fibrous coated formed film 100 has a thickness ranging from about 0.005 to about 0.100 inches, preferably 0.020 inches, the absorbent core has a thickness ranging from about 0.125 to about 1.0 inches, preferably 0.5 inches and the fluid impervious backsheet 107 has a thickness ranging from about 0.00075 to about 0.005 inches, preferably 0.0012 inches.

Figure 7:
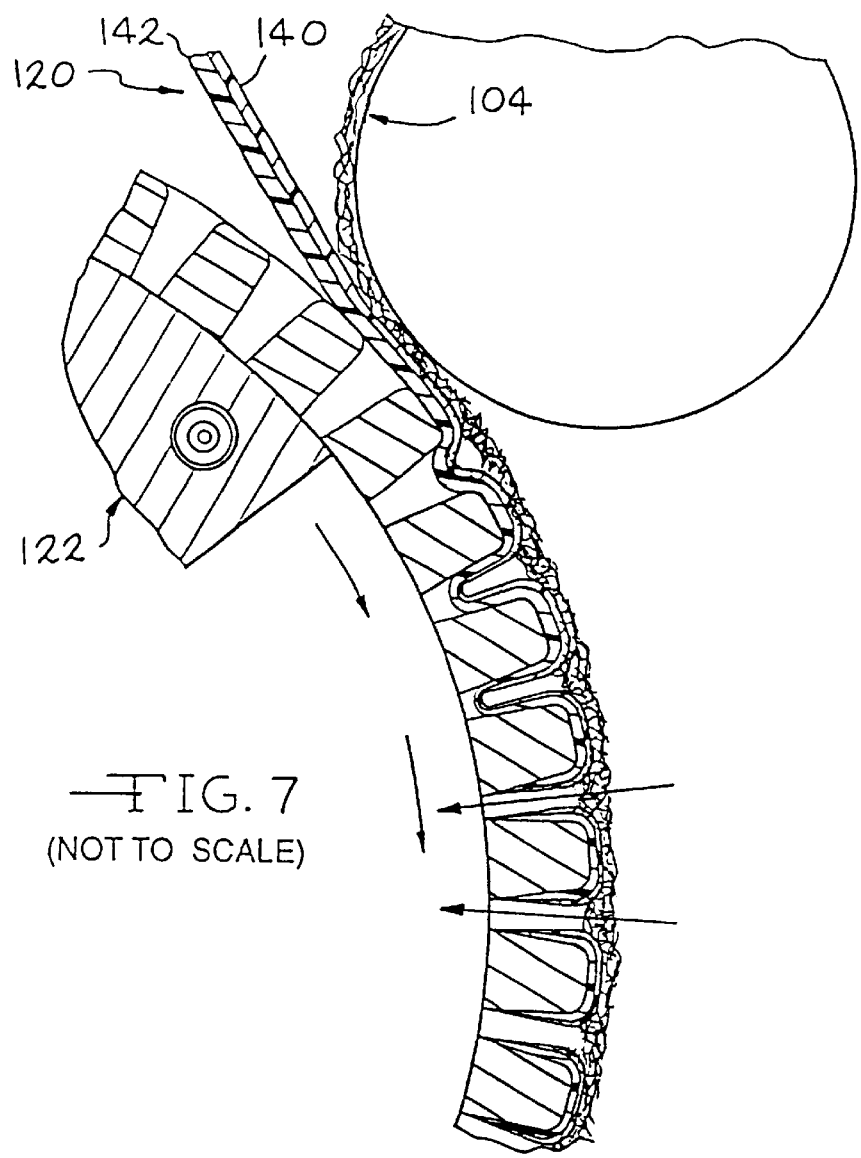
FIG. 7 is a greatly enlarged simplified cross-sectional schematic illustration of a process for producing a fibrous coated formed or perforated film where the film is coextruded such that the top layer of film has a lower melting temperature than the bottom layer and the fibers are either embedded into this softer layer as in FIG. 8A or the fibers are also coextruded with their outer layer being of lower melting temperature than their core layer such that the outer fiber layer and top film layer are melt fused together as shown in FIG. 8B.

Referring now to FIG. 7, a simplified cross-sectional schematic diagram of a process for producing a surface modified fibrous formed film having two layers is shown. A film 120 is coextruded onto the pressure differential film forming means 122. The film 120 comprises an upper or skin layer 140 and a lower or base layer 142. In the preferred embodiment, the upper layer 140 comprises about 10% to 15% of the total film and is comprised of a material having a melt temperature significantly lower than portion 142. In certain embodiments, the upper layer 140 can comprise ethylene methylacrylate (EMA) which has adhesive properties, without containing any adhesive or glue-type materials. The "adhesive" or sticky top layer 140 allows the fibrous material 100 easily adhere to the film 120. The base layer 142 may comprise a resin containing a surfactant to further aid in providing the film with good fluid acquisition properties (which properties are needed in end use applications such as absorbent articles). The upper layer 140 is coextruded on a upper exposed side of the base layer 142. The upper layer 140 remains soft and molten at the point of interface to allow penetration and mechanical bonding of a fibrous material 100. This two layer surface modified fibrous film is especially useful in end use applications where the physical property requirements of the fabric film structure demand toughness, stiffness or thermal stability. When such formed film structure is necessary, the type of polymer material used for the base layer adds to the toughness and/or thermal stability.

Figures 8A, 8B:
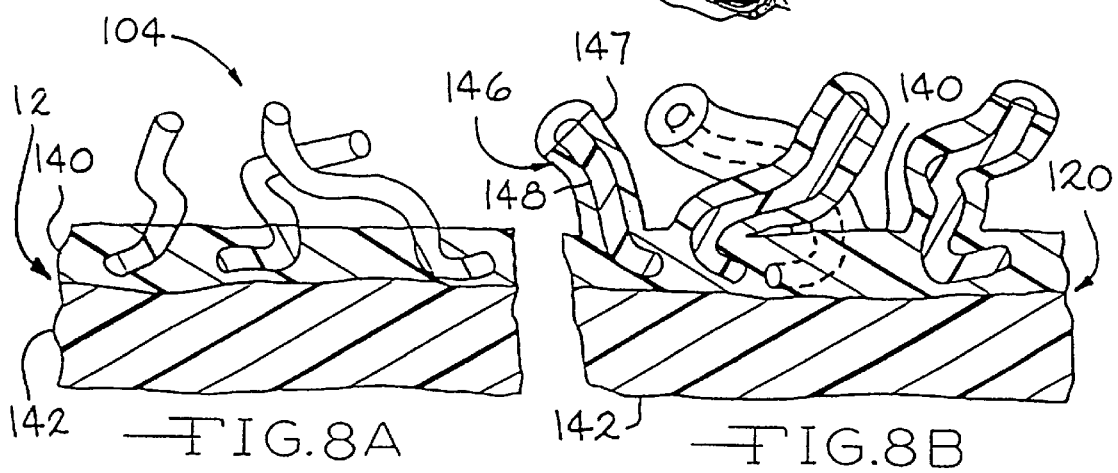
FIG. 8A is a greatly enlarged simplified cross-sectional schematic illustration of fibers having been imbedded and mechanically bonded to the softer, lower melting temperature top layer of a coextruded film.
FIG. 8B is a greatly enlarged simplified cross-sectional schematic illustration of coextruded fibers having their outer layer of softer, lower melting temperature material being melt fused to the softer, lower melting temperature material of the top layer of a coextruded film.

FIG. 8A shows a greatly enlarged simplified cross-sectional illustration of a surface modified fibrous coated formed film comprising the coextruded film 120 shown in FIG. 7 above and having the fibrous material 100 is embedded in the coextruded film 120. The fibrous material 100 is mechanically bonded to the upper layer 140 of the film 120. (If both the upper layer 140 of the film 120 and the fibrous material 100 are of the same or compatible materials, the fibrous material 101 can readily fuse and bond to the upper layer 140 of the film 120). FIG. 88 is a greatly enlarged simplified cross-sectional illustration of a surface modified fibrous formed film comprising the coextruded film 120 shown in FIG. 8 above and coextruded fibers 146 bonded thereto. The coextruded fiber 146 has an outer layer 147 and an inner layer 148. The outer layer 146 is fused to the upper layer 140 of the film 120.

Figure 9:
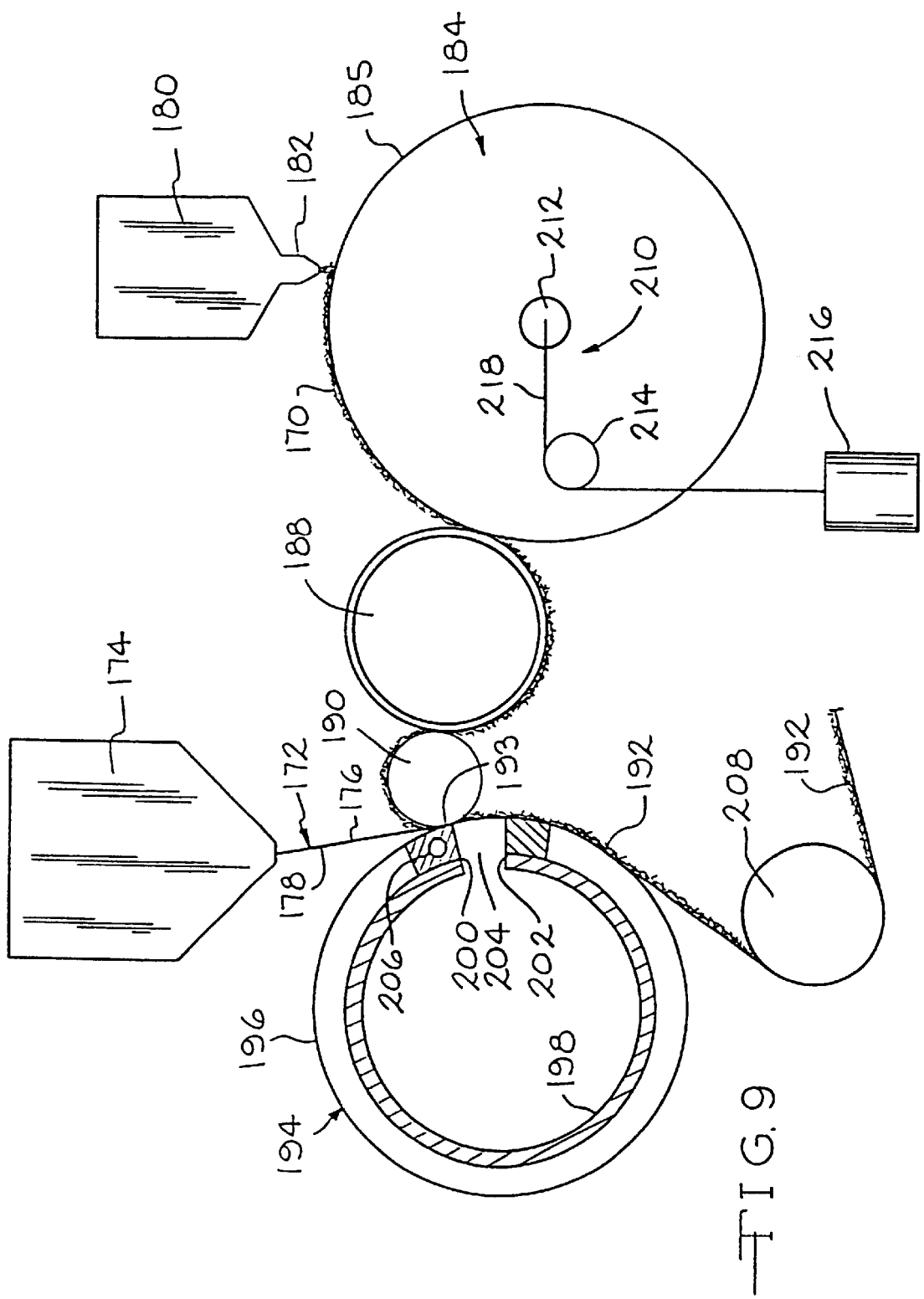
FIG. 9 is a simplified cross-sectional schematic illustration of a process for producing a fibrous coated formed or perforated film.

FIG. 9 shows one embodiment of a method of adhering a low basis weight melt-blown fibrous material 170 onto a film 172. The film 172 is dispensed from a die 174 as a polymeric web. The film 172 has a top surface 176 and a bottom surface 178.

A means 180 for dispensing a predetermined amount of the fibrous material 170 is shown in FIG. 9 as a fibrous forming system. However, it is to be understood that the dispensing means can be a roll (not shown) of a previously formed low basis weight fibrous material 170. If it were a roll, it would be located in the same position as drum 184.

In the embodiment shown in FIG. 9, the fibrous material 170 is dispensed from the dispensing means 180 through a die 182 onto a fiber web delivery means 184. In the embodiment shown, the fiber web delivery means 184 comprises a cylindrical drum 185, a transfer means 188 and an impingement roller means 190. In certain embodiments for a continuous process, it is desired that the fiber web delivery means 184 comprise a cooling drum for accepting melt blown web materials 170 which are formed and then dispensed from the dispensing means 180 and die 182.

The transfer means 188 is in contact with both the drum 185 and the impingement roller means 190. The transfer means 188 can comprise a rubber coated roller to aid in delivering the fibrous material 170 by providing friction such that the impingement roller means 190 transfers the drive force to the transfer means 188 which in turn transfer the drive force to the drum 185 and drives it. The transfer means 188 is positioned adjacent a portion of the drum 185. The fibrous material 170 is moved or transferred from the drum 185 into the stream of film 172 by passing over the transfer means 188 and the impingement roller means 190. In preferred embodiments, the transfer of the fibrous material 170 occurs under zero to near zero tension in order to prevent breakage of the fibrous material 170. In preferred embodiments, very low weight melt-blown non-woven fibrous materials having about 3–5 g/m$^2$ basis weight are effectively laminated or adhered to a film using this method.

The impingement roller means 190 is positioned at a point where the fibrous material 170 contacts the film 172. The impingement roller means 190 can be temperature controlled to prevent melting or sticking of the thin low basis weight fibrous material 170 to the impingement roller means 190 itself. The impingement roller means 190 can either cool or heat the fibrous material 170 and the film 172 to form a laminated film 192 at a point of impingement 193. The laminated film 192 is passed over a film forming means 194. In the embodiment shown in FIG. 9, the film forming means 194 is depicted as a drum having a surface 196 which is highly perforated with apertures (not shown) extending therethrough. The apertures allow fluid, such as air, to pass through the surface 196 of the film forming means 194. The film forming means 194 generally includes a vacuum pressure differential means 198 which creates a pressure differential between the top surface 176 and the bottom surface 178 of the film 172. The film forming means 196 generally includes a leading edge of a seal 200 and a trailing edge of a seal 202 which defines a vacuum chamber 204. When the film forming means 194 is a screen, as shown in the figures herein, it is preferred that the perforated surface 196 rotate over the seals 200 and 202. The vacuum chamber 204 is located within the film forming means and is utilized to create a pressure differential between the top surface 176 and the bottom surface 178 of the film 172. As the film 172 is extruded from the die 174, the film comes into contact with the rotating surface 196 of the film forming means 194. The rotating perforated surface 196 of the film forming means moves continuous portions of the film 172 across a vacuum chamber 204. The pressure differential caused by the vacuum chamber 204 pulls portions of the film 172 which are adjacent apertures of the surface 196. The fibrous material 170 is brought into contact with the film 172 at the point of lamination 193 prior to the leading edge 200 defining the vacuum chamber 204. In certain embodiments, a temperature control means 206 can be positioned at the point where the fibrous material 170 contacts the film 172. In the embodiment shown, the temperature control means 206 is shown as a rod heater. However, it is to be understood that other temperature control means, including other heating and cooling means, can be used to adjust the temperature of the film 172 and the fibrous material 170 at this point. The fibrous material 170 embeds into and/or melt fuses onto the top surface 176 of the film 172. The temperature control means 206 and the temperature control means of impingement roller 190 adjusts the: amount of heat to the film 172 and the fibrous material 170 to counteract any negative heat flux in the film which occurs when the fibrous material contacts the film. A roll 208 can be provided to aid in removing the successive portions of the fibrous formed film from the film forming means. In certain embodiments, it is contemplated that the rod heater 206 can be a cooling rod to remove additional heat from the fibrous formed film 192.

The point of lamination 193 occurs before the film 172 reaches the vacuum chamber 204. The point of lamination 193 can be adjusted such that lamination occurs either farther upstream of the vacuum chamber 204 or closer to the vacuum chamber 204. Factors affecting the optimum point of lamination include the compositions of the fibrous material 170 and the film 172, the thicknesses of the fibrous material 170 and the film 172, and the temperatures at which the fibrous material 170 and the film 172 are delivered to the point of lamination.

The embodiment shown in FIG. 9 is for a continuous process. However, it should be understood that the present invention is also useful with a batch process wherein the fiber delivery means 184 would comprise a roll of previous formed fibrous material. In certain embodiments, it is useful to have a pressure adjusting means 210 which is operatively connected to a center shaft 212. In a continuous process, the center shaft 212 is the center shaft of the drum 185. In a batch process, the center shaft 212 comprises the center portion of a roll of fibrous web. The pressure adjusting means 210 can comprise a pulley 214 and a counter weight 216 which are operatively attached to the center shaft by a cable 218. The pressure adjusting means 210 can comprise air cylinders or oil cylinders or electrical devices, including magnetic or motorized systems for applying pressure. The pressure adjusting means 210 provides constant pressure such that the roll 185 contacts the surface of the transfer means 188 in a constant manner. In a batch process, the tension adjusting means 210 provides constant pressure to contact the surface of a roll of fibrous material onto the surface of the transfer means 188 as the roll of fibrous web diminishes in diameter as the web is being unwound and deposited onto the film 172.

When a batch process in used, the fiber delivery means 184 is a roll of pre-made fibrous material, more particularly a very light web requiring zero tension. The impingement roller means 190 contacts the rotating screen 196 and is thus "driven" at the same speed. The transfer means 188 is a rubber coated roll to provide friction such that the impingement roller means 190 transfers the drive force to the transfer means 188 which in turns transfers the drive force to the fiber delivery means 184, all being driven at virtually the same surface speed. The pressure adjusting means 210 provides constant and proper pressure such that the fiber delivery means 184, the transfer means 188, the impingement roller means 190 and the screen surface 196 keep driving each other as the roll of fibrous material diminishes in size as it is being unwound. In preferred embodiments, the transfer means 188 has a sufficient diameter to provide room for air to enter the vacuum chamber 204 in that the large diameter roll 184 is not located too close to vacuum chamber 204, thus becoming restrictive to the air flow pathway.

Figure 10:
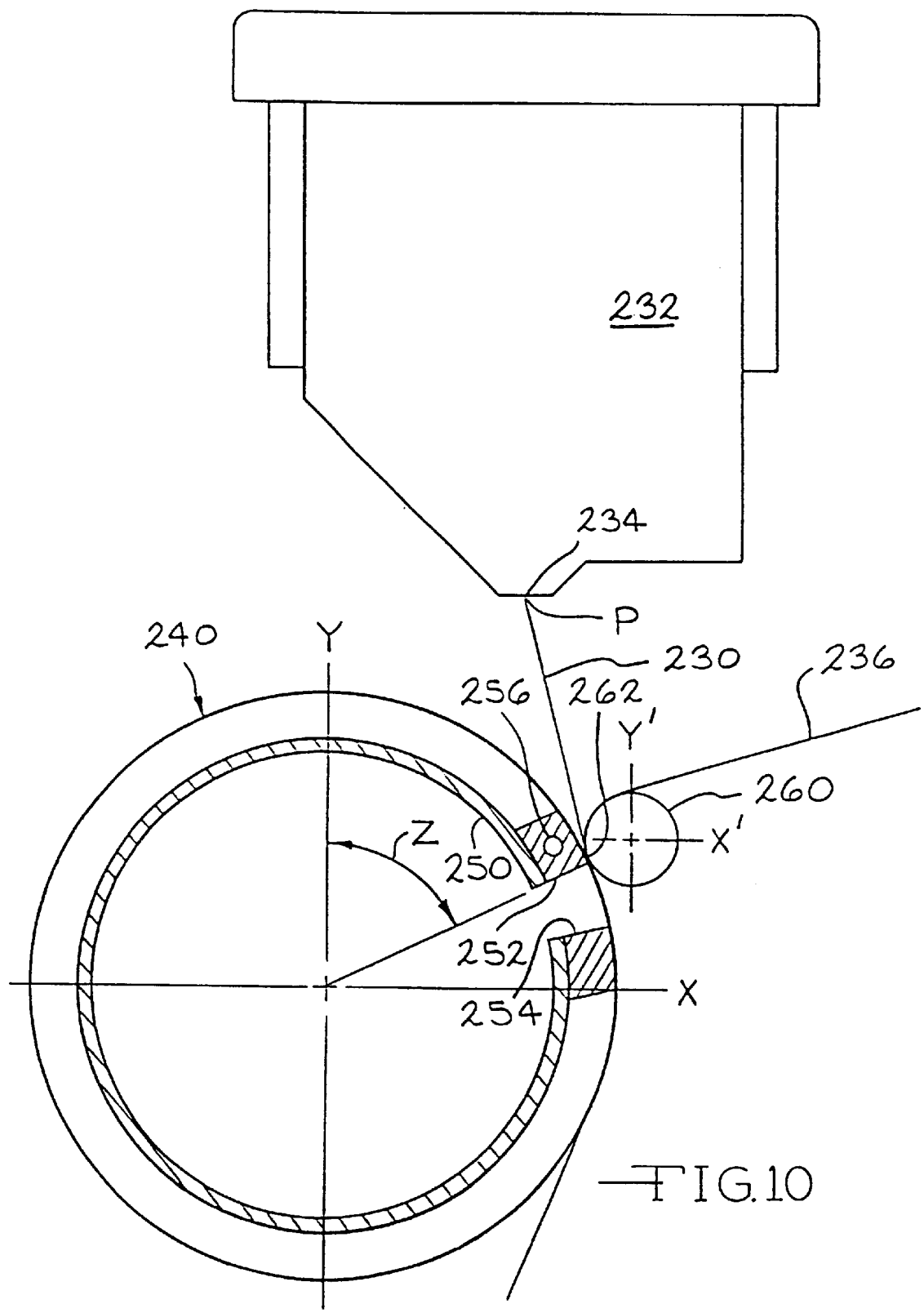
FIG. 10 is a simplified cross-sectional schematic illustration of a process for producing a fibrous coated formed or perforated film.
Figure 11:
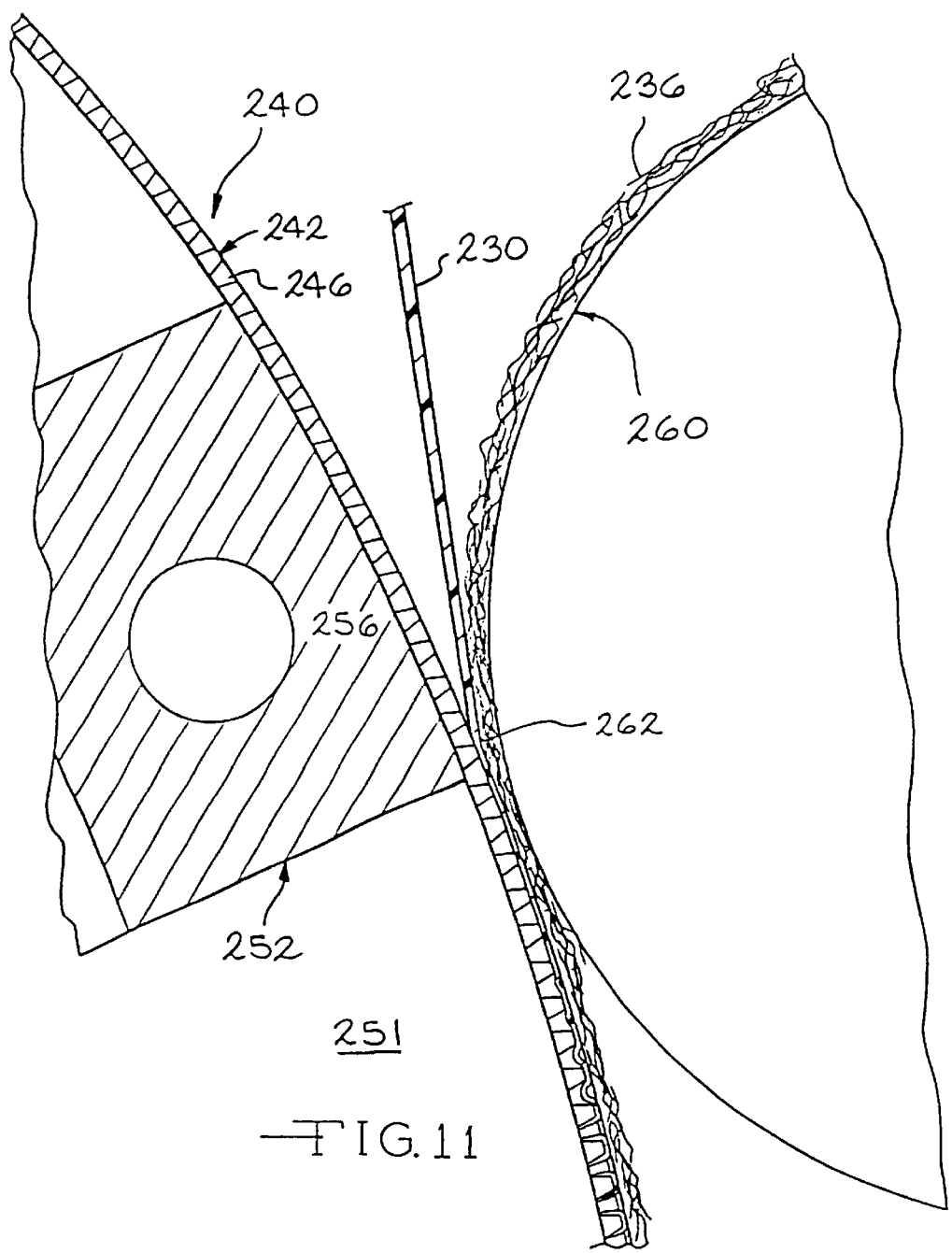
FIG. 11 is an enlargement of an area of impingement of fibrous material onto a polymeric film material for the process shown in FIG. 10.

FIGS. 10 and 11 are a diagrammatic sketches of one embodiment for laminating a low basis weight fibrous material onto a film according to either processes shown in FIGS. 1 and 9 above. FIG. 10 shows various positioning of variables which can be regulated to achieve precise impingement of a fibrous material onto a melt stream of film material. The primary reference point at the die lip is designated as P. The vacuum slot angle is represented as Z, wherein 0° is the vertical and 90° is the horizontal. The X represents the horizontal axis position from point P for the film forming means 240. The Y represents the vertical axis position from P for the film forming means 240. The X' represents the horizontal axis position from P for the impingement roll 260 (either 43 in FIG. 1 or 190 in FIG. 9), while Y' represents the vertical axis position from point P for the impingement roll 260 (43 or 190). A melt stream or molten web 230 is dispensed from a die 232 through a die lip 234. Fibrous material 236 is supplied either from a roll or in a continuous process (not shown). The film 230 is dispensed from the die, preferably at a distance of about 3–4 inches and at an elevated temperature onto a film forming means 240. The film forming means 240 has a surface 242 which is highly perforated with apertures (not shown) extending therethrough. The apertures allow fluid, such as air, to pass through the surface 242 of the film forming means 240. The film forming means generally includes pressure differential means or vacuum chamber 251 which generally defines a leading edge seal 252 and a trailing edge seal 254. The leading seal 252 and trailing seal 254 defining the vacuum chamber 251 are stationary. The screen 242 rotates over the stationary vacuum chamber 251 and seals 252 and 254. A temperature control means 256 is position at a point adjacent the leading edge 253. In the embodiment shown, the temperature control means 256 is shown as a heated rod. However, it is to be understood that other temperature control means, including heating or cooling means, can be used to adjust the temperature of the film and fibrous material at this point. Fibrous material 236 is brought into contact with the molten web 230 by advancing over an impinging roll 260. The impinging roll 260 either carries a fibrous web or a uniform layer of random or loose fibers.

Figure 12:
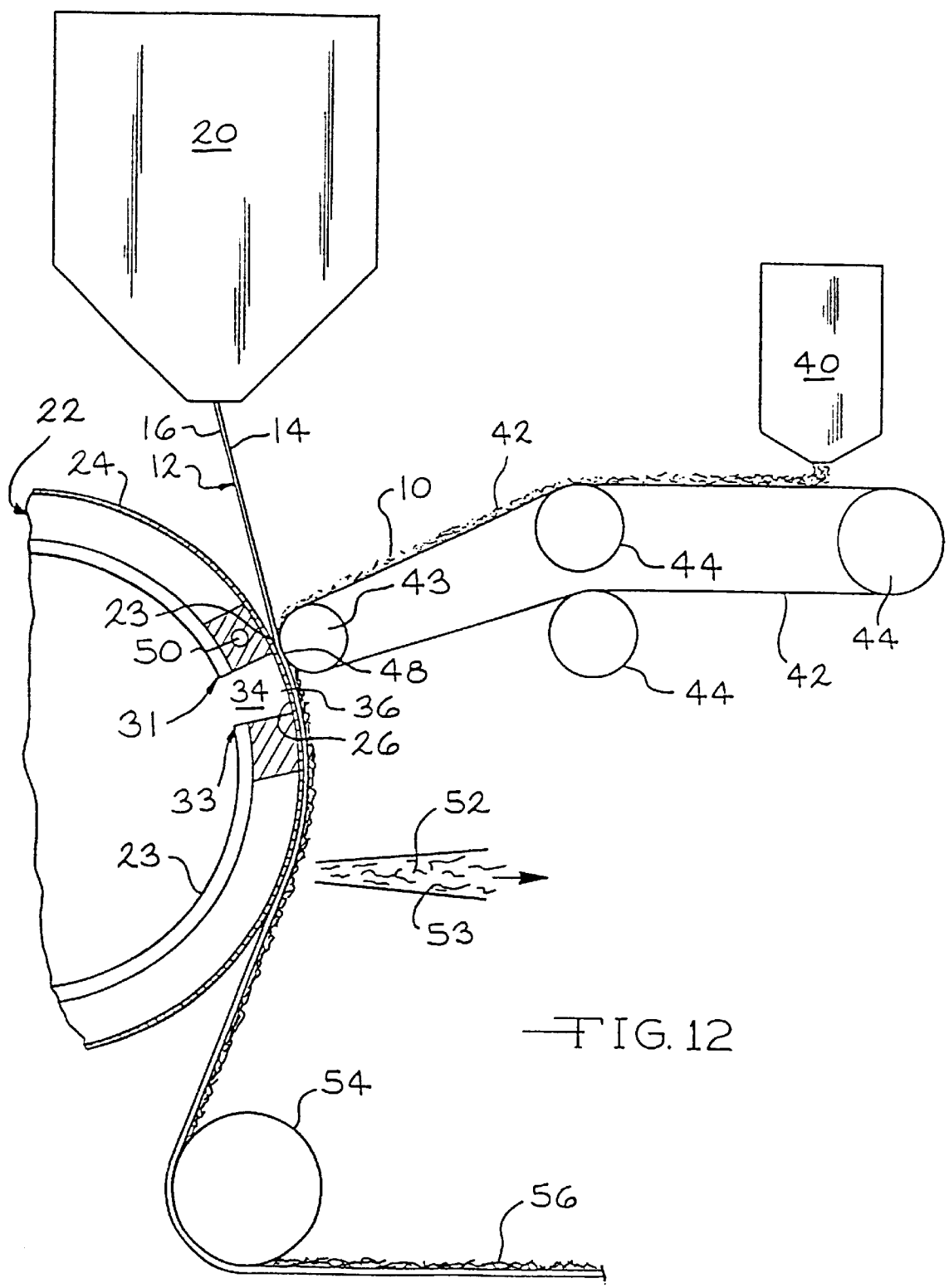
FIG. 12 is a simplified cross-sectional schematic illustration of another process for producing fibrous coated formed or perforated film.

In FIG. 12, the randomly loose fibers are applied or dispensed from the conveyor 42 onto the film 12 under zero to near zero tension. In a preferred embodiment, the fibers 10 are delivered at an angle rather than directly in front of the vacuum chamber 34. Supplying the fibers at an angle helps keep the pathway of the airstream into the vacuum chamber 34 clear and uninhibited so a sufficient vacuum can be drawn to form the three-dimensional structures or apertures in the fiber coated film material.

The dispensing means 40 can be a fiber carding device or a fiber air-laying system, a gravimetric and/or vibratory system, or other type of system which feeds and meters a predetermined amount of fibrous material. In the embodiment shown in FIG. 12, for example, the dispensing means 40 generally comprises an endless conveyor belt 42, an impingement roller 43 and a plurality of low inertia rollers 44. The conveyor belt 42 can comprise a rubber coated belt such that static energy is used to help the fibers adhere to the belt during conveying of the fibers 10 toward and onto the film material 12. Rollers 43 and 44 can also be driven rollers such that the speed of the conveyor belt can be controlled to match the speed of the screen 24. In other embodiments (as shown in FIG. 9), the dispensing means 40 can comprise a means for forming and delivering a web of nonwoven fibrous material.

According to the present invention, a position of the impingement roll 260 is dependent upon the desired thermal balance. Various possibilities exist for the manipulation of the parameters required in order to achieve a thermal balance. For example, to achieve the desired input heat of the melt stream 230 at a desired impingement point 262, it is possible to vary both the length of the melt stream 230 and the temperature of the molten web as it exits the die lip 234. Since convective losses of heat are experienced as the molten web is suspended in the atmosphere, more length of film means that there is more heat loss, thus a higher exit temperature would compensate for such heat loss. However, the inverse is also true, a shorter length of molten material gives off less heat so the exit temperature of the melt stream from the die 234 could be lowered. It is to be understood that various polymers have different melt temperature and that the length of the molten stream between exiting the die lip and the impingement point can be varied based on the. parameters defined by the use of a particular polymer. Thus, entering the impingement point in the molten state (that is above the temperature of melting) will depend on the melting temperature of the specific polymer in use at the time.

In another example, the thermal balance (which is achieved by the heat transfer that occurs) requires a certain amount of time to lapse. Thus, the distance between the leading seal edge 252 and the trailing seal edge 254 defines a predetermined vacuum gap distance. Hence, the time is determined by the speed of rotation of the screen 242 over the vacuum chamber 250 and the distance between the leading edge 252 and trailing edge 254 of the vacuum chamber 250. Therefore, if one wishes the process to go faster, one must increase the distance between the leading edge and the trailing edge in order to maintain a minimum desired time factor necessary for the proper heat transfer to occur. The parameters defined herein relating to melt temperatures, melt stream length and vacuum slot distance are one set of combinations which can be varied in order to achieve the film of the present invention. However, other parameters relating to impingement point positioning can also be varied, as described herein.

EXAMPLE 1

A polymer having a 0.922 g/cc density and a 3.8 Melt Index, blended with 4% $TiO_2$ white pigment drawn to a 1.00 finished caliper and a spun bonded polypropylene nonwoven web of about 11 g/sq.yd.wt. with a loft of about 0.8 mil, were laminated or melt bonded together. The melt temperature of the polymer ranged from about 450° to about 500° F. and preferably about 475° F. and the melt length (as measured from the point P to impingement point 262) ranged from about 2½ to about 5½ inches and in preferred embodiments about 4 inches. The vacuum slot distance between the leading edge and trailing edge ranged from about 1.125 to about 1.75 inches and preferably about 1.5 inches in length.

Referring now to FIG. 11 in particular, the film 230 and the fibrous material 236 come together to impinge at point 262 directly at about the leading edge 252. In preferred embodiments, the point of impingement 262 ranges from the leading edge 252 to a distance upstream for about ⅛ inch. In preferred embodiments, the melt stream 230 contacts the fibrous material 236 and the screen 242 at approximately the same time. Since the simultaneous contacting of the melt stream fibrous material 230 and screen 242 is difficult, if not impossible, to achieve, in preferred embodiments, it is desired that the molten stream 230 contact the fibrous material 236 first since the fibrous material 236 puts less mass in contact with the melt stream 230 such that less damaging heat loss occurs. If the stream 230 contacts the screen 242 first, then dramatic heat loss begins to occur and more heat compensation is necessary. The range of contact of molten stream to the fibrous material ranges preferably from the leading edge 252 to a distance of about 3/16 inch upstream on the molten web and preferably 1/8 inch.

Another parameter is the compression or pressure of the fibrous material 236 against the film 230 while the fibrous material 236 and film 230 are in a contact point 262 between the screen 242 and the impingement roll 260. The optimum compression is about 50% of the ambient loft of the fibrous material 236. That is, if the web or mass of independent fibers has a loft of about X inches at ambient or "room" conditions of barometric pressure and temperature, then ideally the fibrous material 236 will be compressed at the impingement point from about 25 to about 75% of its ambient loft (i.e., 0.5X±0.25X). In certain embodiments, the resiliency of the fibers under compression (i.e., the fact that the fibers tend to straighten back up to their original shape and position they had prior to any compression at point 262) will force a portion of their fiber length to embed in the soft molten polymer directly beneath them. Too much compression will force too many fibers to deeply embed or distort and the desired cloth-like characteristics of the end product are lost. In addition, too much compression causes problems such as having the impingement roll 260 bounce, which then causes provide an uneven lamination of the fibrous material 236 onto the molten material 230. Alternatively, if too little compression is used, there is not enough force to cause sufficient embedding of the fibrous materials such that the fibrous material is not laminated adequately and will fall or peel off the end product.

FIGS. 10 and 11 also show the angle between the impingement point and the point "P" at which the molten web leaves the die 234. If the angle is too obtuse, then the film might touch the screen too early. If the angle of the melt stream is too acute, it will then contact the fibrous material significantly prior to the desired impingement point 262 such that it is too hot and too molten and may damage and distort the fibrous material; or, if not that, it may surrender too much heat too early to the fibrous material.

The basis weight of a melt blown fibrous web material preferably ranges from about 3 to about 15 g/m$^2$; in certain embodiments preferably ranges from about 8–12 g/m$^2$. The lower basis weight melt blown fibrous web materials are particularly useful in producing a high quality fibrous texture on the top surface of the film. Further, the fiber diameter of the melt blown fibers can be varied. Thicker fibers are less likely to be pulled into the apertures in the film. However, in certain embodiments thicker fibers may form entangled masses of fibers on the top surface of the film. The pressure differential is preferably adjusted when using finer diameter fibers so that a turbulent fibrous stream is not created before the finer diameter fibers contact the top surface of the film. In addition to varying the pressure differential, the distance between the point where the fibrous material is dispensed onto the top surface of the film can be adjusted to control the amount of fibers fusing onto the forming film.

In certain embodiments, melt blown webs of fibrous material are made at a point near the film forming process and then directly bonded to the forming film. It has been found that both webs having lower basis weights of about 3 or 4 to about 5 g/m$^2$ and heavier webs of about 8–15 g/m$^2$ can be utilized. These webs can be applied to the top surface of the film at the point of perforation using the methods shown in FIGS. 1, 9 and 12 as described herein.

It is within the contemplated scope of the present invention that the fibrous material can substantially cover the entire surface of the film, or alternatively, the fibrous material can be bonded to selective portions of the film. The selective zones or portions of the film can be readily determined by functional patterns required by the end use application. In applications where selective coverage of the fibrous material is to be bonded to the film, non-woven webs can be slit, unwound and delivered or channeled over the selected portions of the formed film.

The formed film can be made with different screen patterns having different percentages of open areas hole sizes, hole geometries, materials and surface coatings and treatments. It is also contemplated that various blends of resins used to formulate the film can be used to achieve the desired qualities of the end use product.

The amount of pressure differential across the top surface and bottom surface of the film can be either increased or decreased to prevent the fibrous material from being pulled though the apertures in the film and to provide a more fibrous texture on the top surface of the film. The pressure differential level is regulated such that there is proper aperture formation.

Various melt blown webs and spun-bonded webs are thermally bonded which increases the web strength surface stability and web integrity. The thermal bonding also decreases fiber mobility. When thermally bonded melt blown webs are utilized, fewer fibers are pulled into the film apertures. The thermally spun-bonded webs also have a high resistance to surface abrasion. In various embodiments, the use of an ultrasonic thermal bonding means (not shown) prior to transfer of the web to the film surface aids in improving the integrity of the melt blown web.

In certain embodiments, melt blown non-woven materials are especially attractive due to the low cost of producing melt blown materials.

In various embodiments, it is useful to use a thermally or ultrasonically bonded low basis weight melt blown non-woven material. The thermal or ultrasonic bonding of the melt blown web increases the strength of these low weight webs which in turn decreases the chance of web breakage during unwinding, web transfer and lamination. In certain embodiments, the thermal bonded and ultrasonic bonded web have increased surface stability and fiber-to-fiber bonding which prevents fibers in the web from being pulled into the film apertures at the point of perforation.

EXAMPLE 2

Table 1 provides an example of a 1 mil formed film and a 4 g/m$^2$ melt blown non-woven web. As can be seen from the data, the tensile strength, % of elongation, 5% stress and porosity of the web show that the web has good converting properties. The % runoff, rewet, modulus and drain rate all show the fluid acquisition properties of the non-woven web to be suitable for many end uses. Preferably, the products prepared in accordance with the present invention have a runoff, by volume from about 0 to about 3%. The preferred percentage runoff being about 0 to about 1.5%.

In addition, the rewet rate of the film of the present invention is especially low and in preferred embodiments ranges from about 0.03 g to about 0.1 g. Further, the drain rate or how fast the liquid flows through the apertures in the film is a significant improvement over other film materials.

TABLE 1

| PRODUCT PROPERTY | | |
|---|---|---|
| Low Load Thickness (mils) | | 15.91 |
| Tensile (lbs) | MD | 1.32 |
| | TD | 0.97 |
| (Grams) | MD | 600 |
| | TD | 440 |
| Elongation (%) | MD | 135 |
| | TD | 306 |
| 5% Stress (Grams) | MD | 160 |
| | TD | 70 |
| Porosity (CFM) | | 135 |
| Runoff (%) | | 0 |
| Rewet (grams) | | 0.05 |
| Modulus, Low strain (kg/cm) | | 1.287 |
| Modulus 1% (Kpa) | MD | 68922 |
| Drain Rate (kg/M$^2$) | | 511 |

While the present invention has been described primarily in the context of a topsheet for a disposable absorbent product, it is recognized that the present invention may also be practiced to advantage in many other applications and environments. It will be obvious to those skilled in the art that various changes and modifications can be made without departing from the spirit and scope of the present invention, and it is intended to cover the claims appended hereto. All such modifications are within the scope of this invention.

What is claimed is:

1. A composite material comprising:
    a polymeric film having a first side defining a planar surface, a second side having a plurality of three-dimensional structures extending outwardly from said second side, and a plurality of apertures, each of said apertures having an inlet on the first side and said apertures extending through the composite material and having at least a portion of each aperture defined by a sidewall extending from the first side of the polymeric film through one of said three-dimensional structures extending outwardly from the second side of the polymeric film; and
    a plurality of individual loose microfibers coupled substantially only to said first side of said polymeric film and to at least a portion of each of said sidewalls of the apertures extending through the polymeric film with a substantial portion of the inlet to the apertures not bridged by the microfibers and remaining open for the passage of fluid therethrough;
    wherein a majority of the individual loose microfibers have at least one end extending from said polymeric film.

2. An absorbent article comprising a topsheet formed of the composite material of claim 1, an absorbent pad and a fluid impervious backsheet.

3. The composite material of claim 1 wherein a portion of each of said individual loose microfibers is mechanically embedded into said first side of said polymeric film.

4. The composite material of claim 1 wherein each of said individual loose microfibers comprises an inner layer substantially surrounded by an outer layer.

5. The composite material of claim 4 wherein said outer layer comprises a first polymer with a first melt temperature, and said inner layer comprises a second polymer with a second melt temperature higher than said first melt temperature.

6. The composite material of claim 5 wherein said first melt temperature is substantially the same as a melt temperature of said polymeric film, and wherein a portion of said outer layer of each of said individual loose microfibers is melted to said first side of said polymeric film.

7. The composite material of claim 6 wherein a portion of each of said individual loose microfibers is mechanically embedded into said first side of said polymeric film.

8. The composite material of claim 3 wherein a majority of said individual loose microfibers are embedded into said polymeric film in such a manner that said polymeric film is in contact with greater than about ninety degrees of a circumference of a each of said individual loose microfibers.

9. The composite material of claim 1 wherein said sidewall of each of said protuberances converges from said first side to said second side.

10. The composite material of claim 3 wherein said polymeric film comprises polyethylene, and said individual loose microfibers comprise a material selected from the group consisting of polypropylene, polyester, and blends of polypropylene and polyester.

11. A composite material comprising:
    a polymeric film having:
    a first layer having a first side, a second side, and a first melt temperature;
    a second layer having a first side defining a planar surface, a second side having a plurality of three-dimensional structures extending outwardly therefrom, said second layer having a second melt temperature higher than said first melt temperature, and said first side of said second layer being coupled to said second side of said first layer;
    a plurality of apertures extending through the composite material from said first side of said first layer through said second side of said second layer, each of said apertures being at least partially defined by a sidewall extending from the first side of said second layer through one side of said three-dimensional structures of said second layer, each of said apertures having an inlet on the first side; and
    a plurality of individual loose microfibers coupled substantially only to said first side of said first layer and to at least a portion of said sidewalls of the apertures, with a substantial portion of the inlet to the apertures not bridged by the microfibers and remaining open for the passage of fluid therethrough;
    wherein a majority of the individual loose microfibers have at least one end outwardly extending from said polymeric film.

12. The composite material of claim 11 wherein a portion of each of said individual loose microfibers is mechanically embedded into said first side of said first layer.

13. The composite material of claim 11 wherein each of said individual loose microfibers comprises an inner layer substantially surrounded by an outer layer.

14. The composite material of claim 13 wherein said outer layer comprises a third polymer with a third melt temperature, and said inner layer comprises a fourth polymer with a fourth melt temperature higher than said third melt temperature.

15. The composite material of claim 14 wherein said third melt temperature is substantially the same as said first melt temperature of said first layer, and wherein a portion of said outer layer of each of said individual loose microfibers is melted to said first side of said first layer.

16. The composite material of claim 15 wherein a portion of each of said individual loose microfibers is mechanically embedded into said first side of said first layer.

17. The composite material of claim 12 wherein a majority of said individual loose microfibers are embedded into said first layer in such a manner that said first layer is in contact with greater than about ninety degrees of a circumference of a each of said individual loose microfibers.

18. The composite material of claim 11 wherein said sidewall of each of said protuberances converges from said first side of said first layer to said second side of said second layer.

19. The composite material of claim 11 wherein said first layer comprises from about ten percent to about fifteen percent of said polymeric film.

20. The composite material of claim 11 wherein said first layer comprises ethylene methylacrylate.

21. The composite material of claim 11 wherein said second layer comprises a surfactant.

22. The composite material of claim 11 wherein said second layer comprises a polymer that imparts toughness, stiffness, or thermal stability to said polymeric film.

23. An absorbent article comprising a topsheet formed of the composite material of claim 11, an absorbent pad, and a fluid impervious backsheet.

24. The composite material of claim 1 wherein said protuberances are arranged in a predetermined pattern.

25. The composite material of claim 11 wherein said protuberances are arranged in a predetermined pattern.

26. The composite material of claim 1 wherein said individual loose microfibers are selected from from the group consisting of polyesters, polyolefins, acrylics, rayons, cottons, and blends of the same.

27. The composite material of claim 11 wherein said individual loose microfibers are selected from from the group consisting of polyesters, polyolefins, acrylics, rayons, cottons, and blends of the same.

28. The composite material of claim 1 wherein said individual loose microfibers are not entangled.

29. The composite material of claim 11 wherein said individual loose microfibers are not entangled.

30. The composite material of claim 1 wherein said individual loose microfibers have a temperature of crystallinity higher than the temperature of crystallinity of said first layer and said second layer of said polymeric film.

31. The composite material of claim 11 wherein said individual loose microfibers have a temperature of crystallinity higher than the temperature of crystallinity of said first layer and said second layer of said polymeric film.

* * * * *

UNITED STATES PATENT AND TRADEMARK OFFICE
CERTIFICATE OF CORRECTION

PATENT NO. : 6,242,074 B1
DATED : June 5, 2001
INVENTOR(S) : Paul E. Thomas

It is certified that error appears in the above-identified patent and that said Letters Patent is hereby corrected as shown below:

Title Page, Item [54] and Column 1, lines 1-4,
Title, please delete "PROCESS TO MELT BOND FIBERS ONTO THREE-DIMENSIONAL FORMED FILM TO ACHIEVE A CLOTH-LIKE TEXTURE AND THE FILM PRODUCED THEREBY" and insert -- COMPOSITE MATERIAL HAVING IMPROVED CLOTH-LIKE TEXTURE AND FLUID TRANSFER PROPERTIES --

Title Page,
Item [56], References Cited, U.S. PATENT DOCUMENTS, insert:

| | | | |
|---|---|---|---|
| -- 5,422,172 | 06/1995 | Wu | 428/230 |
| 5,660,788 | 08/1997 | Gray, et al. | 264/504 |
| 5,567,376 | 10/1996 | Turi, et al. | 264/455 |
| 5,614,283 | 03/1997 | Pontis, et al. | 428/131 |
| 5,731,061 | 06/1998 | Bezier | 428/131 |
| 5,733,628 | 03/1998 | Pelkie | 428/138 --. |

FOREIGN PATENT DOCUMENTS, insert:

| | | | |
|---|---|---|---|
| -- EP 0642 330 | 03/1995 | EPO | |
| GB 2267055 | 11/1993 | UK | --. |

Column 2,
Line 17, after "use" insert -- in --.
Line 17, delete "product" and insert -- products --.

Column 5,
Line 56, after "which" insert -- is --.

Column 6,
Line 10, delete "23" and insert -- 28 --.
Line 25, delete "about 25" and insert -- about .25 --.
Lines 39 and 42, after "adjacent" insert -- to --.

Column 7,
Lines 36 and 49, delete "Differential Scanning Calorimeter" and insert -- differential scanning calorimeter --.

UNITED STATES PATENT AND TRADEMARK OFFICE
CERTIFICATE OF CORRECTION

PATENT NO. : 6,242,074 B1
DATED : June 5, 2001
INVENTOR(S) : Paul E. Thomas

It is certified that error appears in the above-identified patent and that said Letters Patent is hereby corrected as shown below:

Column 9,
Line 4, after "not" insert -- to --.

Column 10,
Line 14, after "3" insert -- ) --.
Line 45, delete "An as" and insert -- Also a --.
Line 57, delete "using.polypropylene" and insert -- using polypropylene --.

Column 11,
Lines 20, 23, 25, 29 and 32, delete "fiber 90" and insert -- fiber 97 --.
Line 44, after "process", delete "that".

Column 12,
Lines 24, 32, 42, 43, 46 and 47, delete "material 100" and insert -- material 104 --.
Line 29, after "coextruded on" delete "a" and insert -- an --.
Line 48, delete "Fig. 88" and insert -- Fig. 8B --.

Column 13,
Line 43, delete "means 196" and insert -- means 194 --.

Column 14,
Line 5, delete "the: amount" and insert -- the amount --.
Line 46, delete "process in" and insert -- process is --.
Line 65, before "diagrammatic" please delete "a".

Column 15,
Line 29, delete "is position" and insert -- is positioned --.

Column 16,
Line 60, delete "Since the simultaneous contacting of the melt stream fibrous material 230 and screen 242 is difficult," and insert -- Since the simultaneous contacting of the melt stream 230, fibrous material 236, and the surface 242 is difficult, --.

Column 17,
Line 25, after "causes" delete "provide".

UNITED STATES PATENT AND TRADEMARK OFFICE
CERTIFICATE OF CORRECTION

PATENT NO. : 6,242,074 B1
DATED : June 5, 2001
INVENTOR(S) : Paul E. Thomas

It is certified that error appears in the above-identified patent and that said Letters Patent is hereby corrected as shown below:

Column 21,
Line 5, delete "of a each" and insert -- of each --.

Signed and Sealed this

Eleventh Day of May, 2004

JON W. DUDAS
*Acting Director of the United States Patent and Trademark Office*